(12) United States Patent
Schwartz

(10) Patent No.: US 7,670,381 B2
(45) Date of Patent: Mar. 2, 2010

(54) PROSTHESIS FOR INTERPOSITIONAL LOCATION BETWEEN BONE JOINT ARTICULAR SURFACES AND METHOD OF USE

(76) Inventor: Marvin Schwartz, 28 Chieftain Crescent, Toronto, Ontario (CA) M2L 2H4

( * ) Notice: Subject to any disclaimer, the term of this patent is extended or adjusted under 35 U.S.C. 154(b) by 154 days.

(21) Appl. No.: 11/710,614

(22) Filed: Feb. 26, 2007

(65) Prior Publication Data

US 2008/0208346 A1    Aug. 28, 2008

(51) Int. Cl.
A61F 2/02 (2006.01)
A61F 2/08 (2006.01)
A61F 2/30 (2006.01)

(52) U.S. Cl. ............... 623/17.17; 623/14.12; 623/17.18; 623/23.41

(58) Field of Classification Search ............... 623/14.12, 623/17.17–17.19, 18.11, 21.15, 21.19, 23.12–23.14, 623/23.42–23.43, 23.52, 908
See application file for complete search history.

(56) References Cited

U.S. PATENT DOCUMENTS

| | | | |
|---|---|---|---|
| 3,053,251 A | 9/1962 | Black et al | |
| 3,178,728 A | 4/1965 | Christensen | |
| 3,579,643 A | 5/1971 | Morgan | |
| 4,224,699 A | 9/1980 | Weber | |
| 4,385,404 A | 5/1983 | Sully et al. | |
| 4,502,161 A | 3/1985 | Wall | |
| 4,627,853 A | 12/1986 | Campbell et al. | |
| 4,778,472 A | 10/1988 | Homsy et al. | |
| 4,911,720 A | 3/1990 | Collier | |
| 4,917,701 A | 4/1990 | Morgan | |
| 5,108,441 A | 4/1992 | McDowell | |
| 5,123,927 A | 6/1992 | Duncan et al. | |
| 5,171,322 A | 12/1992 | Kenny | |
| 5,358,525 A | 10/1994 | Fox et al. | |
| 5,401,234 A * | 3/1995 | Libin | 600/24 |
| 5,445,650 A | 8/1995 | Nealis | |
| 5,489,305 A | 2/1996 | Morgan | |
| 5,549,680 A | 8/1996 | Gordon | |
| 5,624,463 A | 4/1997 | Stone et al. | |
| 5,769,891 A | 6/1998 | Clayton | |
| 5,919,232 A * | 7/1999 | Chaffringeon et al. | 424/423 |
| 6,056,777 A | 5/2000 | McDowell | |
| 6,171,340 B1 | 1/2001 | McDowell | |
| 6,206,927 B1 | 3/2001 | Fell et al. | |
| 6,352,558 B1 | 3/2002 | Spector | |
| 6,558,421 B1 | 5/2003 | Fell et al. | |
| 6,629,997 B2 | 10/2003 | Mansmann | |
| 6,648,920 B2 | 11/2003 | Ferree | |

(Continued)

*Primary Examiner*—David Isabella
*Assistant Examiner*—Yashita Sharma
(74) *Attorney, Agent, or Firm*—Riches, McKenzie & Herbert LLP

(57) ABSTRACT

A biocompatible prosthetic device comprising a thin low friction spacer for location to overlie a bone member in an interpositional location between opposed bone joint articular surfaces. The prosthesis is preferably a thin spacer with at least one low friction surface, the spacer being adapted for location about a bone member in an interpositional location between opposed bone joint articular surfaces preferably about a margin of articular cartilage of a bone member's condyle, preferably without any modification of the articular surface of the condyle. One preferred use of a prosthesis is in a human temporomandibular joint as a thin cap-like member fitted closely over the mandibular condyle to be disposed intermediate of the mandibular condyle and the mandibular fossa of the temporomandibular joint.

38 Claims, 15 Drawing Sheets

U.S. PATENT DOCUMENTS

| | | |
|---|---|---|
| 6,652,587 B2 | 11/2003 | Felt et al. |
| 6,827,742 B2 | 12/2004 | Hayes, Jr. |
| 6,994,730 B2 | 2/2006 | Posner |
| 7,141,072 B2 | 11/2006 | Geistlich et al. |
| 7,148,209 B2 | 12/2006 | Hoemann et al. |
| 2003/0023313 A1* | 1/2003 | Byers ................. 623/17.18 |
| 2003/0060885 A1* | 3/2003 | Fell et al. ............ 623/14.12 |
| 2004/0030402 A1* | 2/2004 | Arnin et al. .......... 623/23.12 |
| 2004/0204760 A1 | 10/2004 | Fitz et al. |
| 2004/0236424 A1* | 11/2004 | Berez et al. .......... 623/14.12 |
| 2005/0267584 A1 | 12/2005 | Burdulis, Jr. |
| 2006/0085079 A1 | 4/2006 | Carroll |
| 2006/0149389 A1 | 7/2006 | Romagnoli |
| 2007/0026053 A1* | 2/2007 | Pedrozo et al. ........ 424/443 |
| 2007/0067032 A1* | 3/2007 | Felt et al. ............ 623/14.12 |
| 2007/0100462 A1 | 5/2007 | Lang et al. |

* cited by examiner

PROSTHESIS FOR INTERPOSITIONAL LOCATION BETWEEN BONE JOINT ARTICULAR SURFACES AND METHOD OF USE

SCOPE OF THE INVENTION

This invention relates generally to medical implant devices and, more particularly, to a biocompatible prosthetic device comprising a thin low friction spacer for location to overlie a bone member in an interpositional location between opposed bone joint articular surfaces.

BACKGROUND OF THE INVENTION

Mammalian, and notably human joints, are subject to damage notably from trauma and disease. Both repetitive microtrauma with occurrence more frequently than a capacity for healing and macro-trauma with significant immediate damage which cannot be recoverable by healing can lead to advancing bone damage. Early stage joint trauma and disease which are not healed typically can lead to a spectrum of pathological conditions of minor joint damage, advancing bone damage, degenerative joint disease and osteoarthritis.

Mammalian joints characteristically join a first bone member to a second bone member and include diarthrodial joints particularly those in which load bearing contiguous bone surfaces of each of the first and second bone members are covered with articular cartilage forming a respective margin of each of the first and second bone members. The contiguous bony surfaces of the surfaces which are normally in contact during movement of the joint are to be contrasted with non-contiguous surfaces of the bone members being surfaces which are not normally in contact during movement of the joint. The articular cartilage is provided as an outer layer over the sub-chondral bone, that is, the bone underlying the cartilage on the condyle at the end of the bone member. A condyle is a round projection or rounded articular area which can generally be characterized as a load bearing surface of a bone member. Articular cartilage is very poorly vascularized and, when damaged by trauma or disease, heals extremely slowly.

Most mammalian joints have, in addition to merely opposing bone members and their cartilage, synovial membranes which may provide synovial fluid proximate or intermediate the bearing surfaces and many joints are also provided with, to be divided completely or incompletely, by an articular disk or meniscus typically provided intermediate opposing articular cartilages.

Joint traumas and disease include damage and disease to the synovial membranes and the articular disk and meniscus if present which lead towards destruction and tearing away of the articular disks or meniscus and subsequent damage to the articular cartilage and subsequent bone to bone contact and damage to the sub-chondral bone.

Presently existing techniques for treating advancing bone damage include firstly biological resurfacing for early stages of the bone damage and, secondly, prosthetic replacement for late stages of bone damage. Biological resurfacing techniques for reconstituting the cartilage include debridement, abrasion arthroplasty, drilling, microfracture techniques, autologous chondrocyte transplant techniques and stem cell seeded transplants. Biological resurfacing has numerous disadvantages and is often unsuccessful, notably due to the fact that cartilage is not vascularized, heals extremely slowly and due to the fact that loading to which the cartilage is subjected due to normal use of the joints destroys the cartilage. Thus, biological resurfacing techniques have a high failure rate. Dilemmas which face biological resurfacing include the requirement that joints must move to remain functional yet movement destroys the new cartilage and prevents new cartilage formation. Thus, only extensive protracted and functionally limited rehabilitation is available which results in significant health care and social costs.

Prosthetic replacement is a treatment technique in which, for example, the entire articular cartilage and sub-chondral bone is replaced by a synthetic member. Typically in prosthetic replacement, as for example in the hip which comprises a ball and socket type joint, the ball on one bone member is completely removed and replaced by the synthetic ball and the interior surface of the socket on the other bone member is completely replaced by a new synthetic socket. Prosthetic replacement suffers significant disadvantages that a patient suffers while its natural joint deteriorates to a sufficient extent that surgery is necessary; the surgery is expensive; and the surgery is biologically destructive and irreversible. Moreover, the new joint is destined to failure after a period of time. Huge health care and social costs are associated with prosthetic replacement.

SUMMARY OF THE INVENTION

To at least partially overcome these disadvantages of previously known devices and methods, the present invention provides a thin spacing prosthesis with preferably at least one low friction surface, the prosthesis being adapted for location about a bone member in an interpositional location between opposed bone joint articular surfaces preferably about a margin of articular cartilage of a bone member's condyle, preferably without any modification of the articular surface of the condyle.

The invention also provides a biominetic technique and prosthesis for joints with menisci that have been removed such as the temporomandibular joint or knee joint and a meniscus-like biomimetic technique and prosthesis for joints that do not usually have menisci such as, for example, the hip joint.

An object of the present invention is to provide an improved method for treating bone disorders, deformities and diseases including a prosthesis for use in treatment of bone disease, a method of manufacturing the prosthesis and a surgical method for implantation of the prosthesis.

The present invention particularly provides a method of modification of an orthopaedic joint which joins a first bone member to a second bone member within a mammalian body.

The prosthesis preferably is a thin sheet-like member to overlie contiguous bony surfaces of a first of the bone member. The joint preferably is a diarthroidial joint in which contiguous bony surfaces on each of the first bone member and the second bone member are covered in articular cartilage forming a respective margin of the first bone member and a respective margin of the second bone member. In a preferred embodiment, a thin sheet-like prosthesis is placed to overlie the margin of the articular cartilage of the first bone member with the sheet member conforming to the shape of the margin of the articular cartilage of the first bone member. The prosthesis is preferably coupled to the first bone member at a non-contiguous surface of the first bone member with the prosthesis disposed in between the margin of the articular cartilage of the first bone member and the margin of the articular cartilage of the second bone member. The contiguous bony surfaces of each of the first and second bone members are surfaces which are normally in contact during movement of the joint. The non-contiguous surface of a bone member is a surface which is not normally in contact during movement of the joint.

The sheet-like prosthesis preferably has an inner surface and an outer surface with the inner surface overlying the margin of the articular cartilage of the first bone member in engagement therewith and substantially corresponding in shape to the margin of the articular cartilage of the first bone member. The prosthesis may be a sheet-like member with uniform thickness and therefore the outer surface of the sheet member will also substantially correspond in shape to the margin of the articular cartilage of the first bone member. On the other hand, the prosthesis may have varying thicknesses.

Preferably, the margin of the articular cartilage of the first bone member forms a convexly rounded articular outer surface of the bone member as, for example, of a condyle of the first bone member. The prosthesis may form a cap-like member over such convexly rounded articular outer surface. The outer surface of the prosthesis is preferably smooth and has a coefficient of friction sufficiently low to facilitate movement relative thereto of the articular cartilage forming the margin of the second bone member in normal movements of the joint and reduce friction without wear by engagement. Preferably, the prosthesis also has an inner surface which is smooth and also has a coefficient of friction sufficiently low to facilitate movement relative thereto of the articular cartilage forming the margin of the first bone member and reduce friction without wear by engagement. The inner surface preferably may resist bonding of the articular cartilage on the margin of the first bone member thereto. Preferably, both the outer surface and the inner surface are smooth.

In accordance with a preferred method, a scan such as a CT scan, is made of the body joint and a model, whether computerized and/or a three-dimensional physical model, is made of portions of the bone member to which the prosthesis is to be engaged. The model may either be a model in conformance with the exact shape of the bone member or may preferably be made to have an exterior surface similar to the margin of the articular cartilage but insofar as the articular cartilage may have depressions or the like, the model may be provided with a smooth surface as to eliminate any recesses in the margin due to pathology.

Thus, the model may have an exterior surface similar to the expected margin of the articular cartilage of the first bone member prior to being deformed due to pathology.

In accordance with manufacture of the prosthesis of the present invention, scanning of the bone member about which the prosthesis is to be fitted, may be carried out by conventional technologies. The creation of a model and mechanically forming, for example, a sheet of tantalum about the model is one way of making the prosthesis. However, the manufacture of a model is not necessary and it is possible, for example, to scan the bone member about which the prosthesis is to be fitted and develop a computer generated version of the prosthesis, suitably adapted for example to adjust or avoid irregularities or depressions in the scanned bone and then to directly arrange for manufacture of the prosthesis. For example, where the prosthesis is to be made from metal, this may be accomplished in a variety of known techniques such as, for example, machining, casting, bending, thermoforming, hydroforming and various other specialized metallurgical techniques. Other techniques may involve the use of complex models and moulds which can readily be made from the scan. Insofar as models or moulds are used, additional techniques for forming could include vacuum sputtering and the like. The particular manner of manufacture of the prosthesis is not limited.

The prosthesis may preferably be formed from metal and notably medically acceptable metals which are preferred because of their biocompatibility and of their ability to be selected to be relatively thin yet, to some extent, bear loads under some conditions and, to some extent, have some flexibility. The prosthesis need not be limited to being provided by metals and may, for example, comprise organic biocompatible materials, polymers, and plastic materials such as formed from a sheet or layer of low friction plastic or polymer materials. The material of the prosthesis could be biologic in origin as, for example, in vitro collagen which may be the patient's own cultured cells or biologically engineered product. The materials of the prosthesis may preferably be pliable, but may be rigid. The sheet member may comprise a composite of plastic or polymer materials as, for example, with metals or other materials preferably providing a smooth low friction outer surface as, for example, of metal or a coating such as low friction nylon and the like. Preferably, coatings which may have an inherent low friction or lubricity and biocompatibility.

In one preferred embodiment, the prosthesis may comprise metal and have a thickness in the range of 0.0005 inches to 0.05 inches and, preferably, in the range of 0.001 inches to 0.01 inches and, more preferably, in the range of 0.001 inches to 0.003 inches. Preferred metals are selected from biocompatible metals including, for example, tantalum, zirconium and titanium and alloys thereof.

One method of forming the prosthesis from sheet metal is to scan portions of the first bone member including the margin of the articular cartilage and non-contiguous surfaces of the first bone member approximate thereto, then form a three-dimensional model of the scanned portions and, subsequently, form a planar sheet of material about the model substantially in conformance with the shape of the model. Where the prosthesis is to be metal, a thin sheet or foil of the desired metal may be mechanically placed over the model and formed to conform to the shape of the margin of the articular cartilage over the model.

In use, the prosthesis is positioned within the body so that portions of the prosthesis overlie contiguous bony surfaces of the first bone member. The prosthesis is retained positioned on the bone member against displacement from desired positions and preferably against displacement which may lead to removal. Preferably, the prosthesis is retained positioned on the bone member with some relative movement permitted between the prosthesis and the articular surface of the first bone member and it is believed that such relative movement may be advantageous and renders the prosthesis a preferred biomimetic.

With many configurations of the prosthesis and with particular condyles of the first bone member, the complementary shape alone of the prosthesis and the condyle of the joint may be sufficient to retain the prosthesis on the margin of the articular cartilage of the first bone member in an acceptable relative position. For example, the prosthesis may also be secured to the first bone member by having a shape which sufficiently envelopes the first bone member to resist removal. The prosthesis may be secured to the first bone member by being engaged about a reduced circumference neck of the first bone member leading to larger circumference portions of the bone member. Accomplishment of such circumferential technique for securing the prosthesis may utilize some mechanism for reducing the circumference of the prosthesis on installation including folding, or an inherent resiliency or a ligature such as a wire or strap for engaging about the reduced circumference neck of the bone. Portions of the prosthesis to engage about a reduced circumference neck may have the ability to expand over the larger circumference portions yet return to a reduced circumference as by being elastic, or resilient or having a shape memory. The prosthesis may be capable of being one piece, folded or gathered upon itself to permit insertion arthoscopically to be uncollapsed and unfolded within the body.

It is believed to be preferred that the prosthesis may need merely to be stabilized relative to the non-articular surface of the first bone member, that is, located thereon against removal but with some movement permitted between the prosthesis and the articular surface of the first bone member. Thus, the prosthesis is coupled, secured or stabilized relative the first bone member but preferably not fixated, cemented or glued to the first bone member in a manner which prevents at least some minor relative movement. The prosthesis may be fixedly secured, fixated, secured with fasteners, cemented or glued to the first bone member against any relative movement, however, this is generally not considered preferable.

The prosthesis may be characterized as comprising an interpositional sheath portion of a spacer member which spacer member further includes a coupling portion connected to the sheath portion for coupling the spacer member to the first bone member at the non-contiguous surface of the bone member. The coupling portion may extend from the interpositional sheath portion overlying the contiguous surface of the first bone member to overlie the non-contiguous surface of the bone member. The coupling portion may be secured to the non-contiguous surface of the bone member by various methods. A preferred method uses a circumferential technique and has the coupling portion engaged about a reduced circumference neck of the first bone member leading to a larger circumference portion of the first bone member carrying the contiguous surface to be covered by the interpositional sheath portion. That is, the interpositional sheath portion may overlie contiguous surfaces including enlarged circumference bulbous portions of a bone condyle and the coupling portion may encircle a reduced circumference neck of the condyle.

The coupling portion may be secured to the non-contiguous surface of the bone member by mechanical fasteners such as known threaded surgical screws, preferably coupling or fastening the coupling portion to the non-contiguous surface of the bone member to permit relative movement between the coupling portion and the non-contiguous surface of the first bone member at least preferably between the interpositional sheath portion and the contiguous surface of the first bone member.

The prosthesis in its interpositional position preferably permits physiological loading of forces applied across the joint, that is, loading which is appropriate to healthy, normal functioning of the joint. Preferably, the prosthesis is adapted to distribute loading forces which may be applied to the sheet member on one of its surfaces over an increased area on the other opposite of its surfaces. This can be of assistance in distributing loading which might normally be applied to a damaged area of the bone member or its cartilage to areas adjacent of the bone member or its cartilage which are not damaged. This is believed to avoid continued damage to the damaged areas of the bone member as to its cartilage or underlying bone and will assist in protecting existing cartilage or underlying bone; preserving the same without further damage and facilitating healing. Preferably, the prosthesis assists in absorbing at least some of any load and distributing localized forces of any load over wider areas. The prosthesis may have a memory such that it returns to the shape of the model when deformed from such shape. The prosthesis may be a resilient member which has an inherent bias to return to the shape of the model when deformed from such shape and which resists deformation from the shape of the model. Some deformation of the prosthesis, whether resilient or permanent, in adapting to dynamic loading may be desirable, for example, to avoid having a small surface area location or "high spot" where focused, increased loading may arise if there were no deformation.

The interpositional location of the prosthesis is advantageous since it requires no destruction of existing tissue of the bone member, preferably no modification of the bone member whatsoever. A preferred prosthesis in providing protection, particularly to the margin of the articular cartilage of the first bone member over which it is closely received provides a protective function in the sense that it protects and preserves the underlying cartilage or bone, halts the advance of pathology and provides a respite for cellular repair in the normal healing courses of the underlying articular cartilage and/or bone member.

In some instances, damage to the first bone member whether to the articular cartilage or underlying bone may advantageously be at least partially treated to promote healing, or, repaired as for example by providing grafts, that is, transplanted living tissue surgically implanted and the prosthesis provides a protective outer cover.

The prosthesis in accordance with the present invention has the advantage of being non-destructive in the sense that it preserves existing tissue necessary for healing. This is believed to assist in faster rehabilitation after surgically applying the prosthesis and providing the increased potential for return to normal function. Use of a prosthesis in accordance with the present invention retains future options including removal; resurfacing of the joint; and joint replacement. The prosthesis is useful for joints in younger, more active patients as a first preferred option and does not prevent the use in the future of other treatment processes.

The prosthesis may be preferably inserted in a surgical operation with open arthrotomy, that is, cutting an incision into a joint.

The prosthesis in accordance with the present invention preferably is for insertion in a joint and to be left inserted as for the life of the patient. Since it is believed that since the presence of the prosthesis will assist in permitting cellular repair of the underlying cartilage and bone, it is also possible and appropriate to surgically remove the prosthesis after some period of time when the cartilage and/or bone member has sufficiently repaired itself.

The prosthesis of the present invention may be used in a wide variety of mammalian joints as for humans and, as well, for veterinary practice for animals. Preferred joints are diarthrodial joints which permit relatively free movement including ginglymus (hinge-type) joints; condyloid articulation joints; trochoid (pivot) joints; joints with articular reciprocal rotation; enarthrosis (ball-and-socket) joints; and arthrodia (gliding) joints, but not limited to these joints. The prosthesis may be advantageously used in humans in the temporomandibular joint; ball and socket joints as in the shoulder joints, hip joints; knee joints; ankle joints; carpometacarpal joint of the thumb; wrist joints, carpal joints and most tarsal joints but not limited to use in such joints.

Insofar as the joints may have a synovial membrane, an articular disk or meniscus, the prosthesis of this invention may be utilized whether or not the membrane, articular disk or meniscus is present, intact or removed or altered. The prosthesis may also be used with joints that do not usually have menisci such as the hip joint and can provide, in effect, an artificial meniscus where none was previously.

One preferred use of a prosthesis of the present invention is in a human temporomandibular joint as a thin cap-like member fitted closely over the mandibular condyle to be located intermediate of the mandibular condyle and the mandibular fossa of the temporomandibular joint.

The prosthesis in accordance with the present invention may be customized as to shape to fit a particular condyle of the bone member upon which it is to be placed. The prosthesis may also be customized so as to provide a desired functionality of the prosthesis for the bone member and joint in question. For example, the prosthesis may be customized as to the extent that it has sufficient strength to withstand forces to which it is subjected without any significant deformation or deflection. For example, in the case of a severely damaged bone member, almost no deflection of a central portion of the prosthesis may be desired. The magnitude of the forces to be transferred through the prosthesis at any joint will vary, for example, with greater forces transferred through a knee joint than a temporomandibular joint and, therefore, different thicknesses of the prosthesis will be required to provide similar rigidity. Where a bone member has minimal damage, a thinner prosthesis may be preferred, possibly with increased resiliency.

Having regard to many factors such as to the nature of the material or materials from which the prosthesis is to be made, the nature of the joint and bone member onto which the prosthesis is to be applied; the nature and extent of the damage to the bone member; and the intended protective surface of the prosthesis; the relative shape, thickness, rigidity, resiliency and strength of the prosthesis may be suitably selected by persons skilled in the medical and material sciences arts.

While in the most preferred use of the prosthesis in accordance with the present invention, a first single sheet-like prosthesis is provided over at least part of the margin of the articular cartilage of a first bone member, in accordance with the present invention, it is also possible in the same joint to provide a second prosthesis, namely, a second sheet-like member to overlie at least part of the margin of the articular cartilage of the second bone member preferably with coupling the second prosthesis to the second bone member at a non-contiguous surface of the second bone member with the second sheet member disposed in between the margin of the articular cartilage of the second bone member and the outer surface of the first sheet member.

In one aspect, the present invention provides a method of modification of an orthopaedic joint joining a first bone member to a second bone member within a mammalian body:

the first bone member having a contiguous outer surface which engages with a contiguous outer surface of the second bone member in normal movement of the joint, the method comprising coupling a spacer member to the first bone member to overlie the contiguous outer surface of the first bone member conforming to the shape the first bone member with the sheet member disposed in between the contiguous outer surface of the first bone member and contiguous outer surface of the second bone member.

In another aspect, the present invention provides a prosthesis for use in an orthopaedic joint joining a first bone member to a second bone member within a mammalian body, wherein the joint is a diarthrodial joint in which contiguous bony surfaces on each of the first and second bone are each covered with articular cartilage forming the respective margin of the first and second bone members;

the prosthesis comprising an interpositional sheath portion, the sheath portion comprising a thin sheet member having an inner surface and an outer surface, the inner surface of the sheet member conforming to the shape of the outer surface margin of the articular cartilage such that the sheath potion is adapted to over lie the outer surface of the articular cartilage of the first bone member, the sheath portion adapted to be disposed in between the outer surface of the articular cartilage of the first bone member and the outer surface of the articular cartilage of the second bone member.

BRIEF DESCRIPTION OF THE DRAWINGS

Further aspects and advantages of the present invention will become apparent to one skilled in the art upon reading the following specification and the following drawings.

DETAILED DESCRIPTION OF THE DRAWINGS

Figure 1:
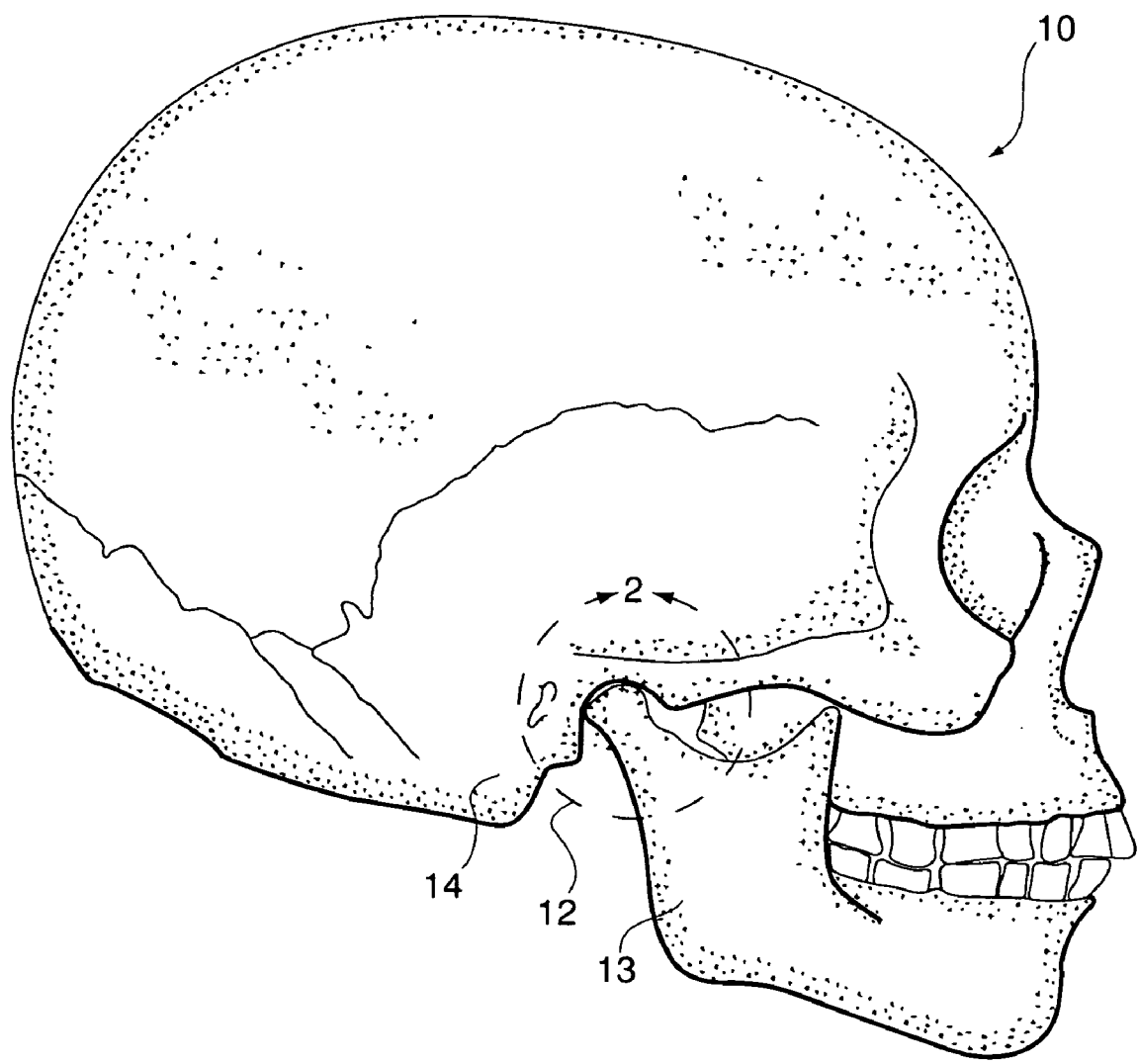
FIG. 1 is a side view of a human skull illustrating the natural environment of a temporomandibular joint.
Figure 2:
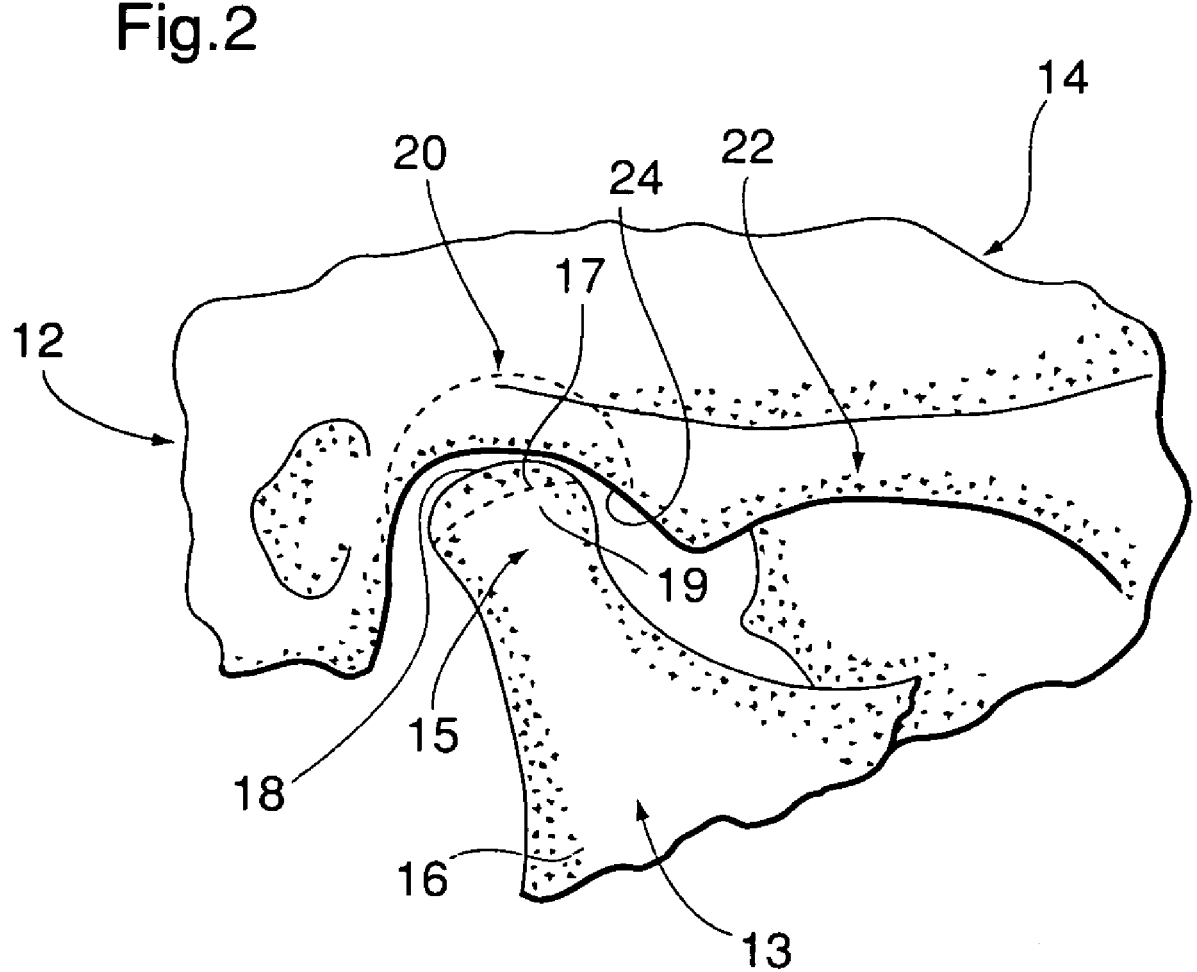
FIG. 2 is an enlarged side view illustrating the temporomandibular joint region shown in FIG. 1.
Figure 3:
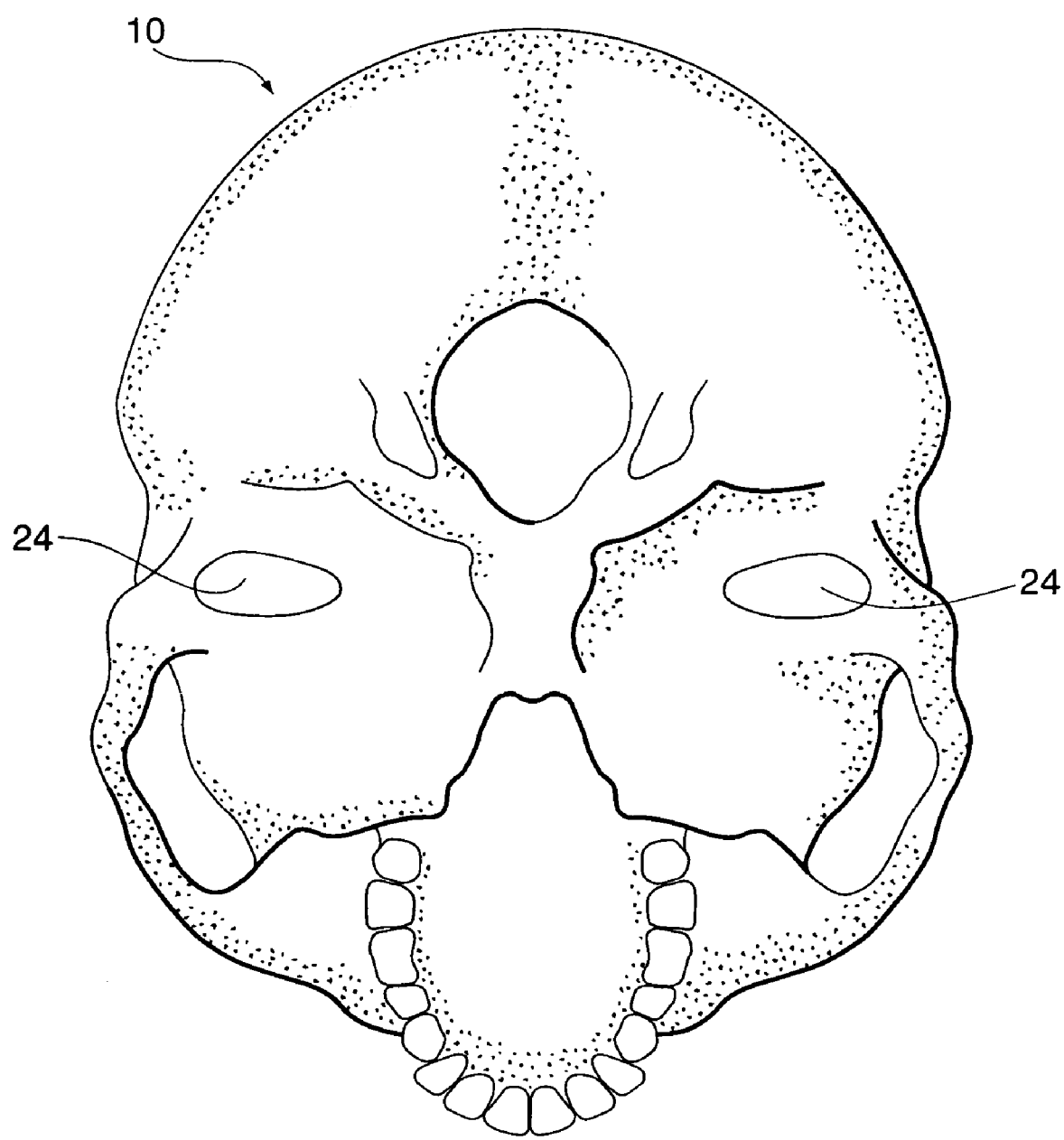
FIG. 3 is a bottom view of a human maxilla illustrating a natural mandibular fossa of a temporomandibular joint.

Referring now to FIG. 1, there is shown a side view of a human skull 10 illustrating the natural environment of a temporomandibular joint region 12. The temporomandibular joint region 12 is shown in enlarged fashion in FIG. 2 as including a mandible 13 and a temporal bone 14. As seen in FIG. 2, the mandible 13 includes a condyle 15 which is a natural protrusion of the ramus 16. The condyle 15 is further shown to include an articular surface 18 which is naturally of a generally rounded convex configuration. The temporomandibular joint region 12 also includes a mandibular fossa 20 which is a region adjoining the zygomatic arch 22. The mandibular fossa 20 includes an articular surface 24 which is of a generally rounded concave configuration.

Figure 5:
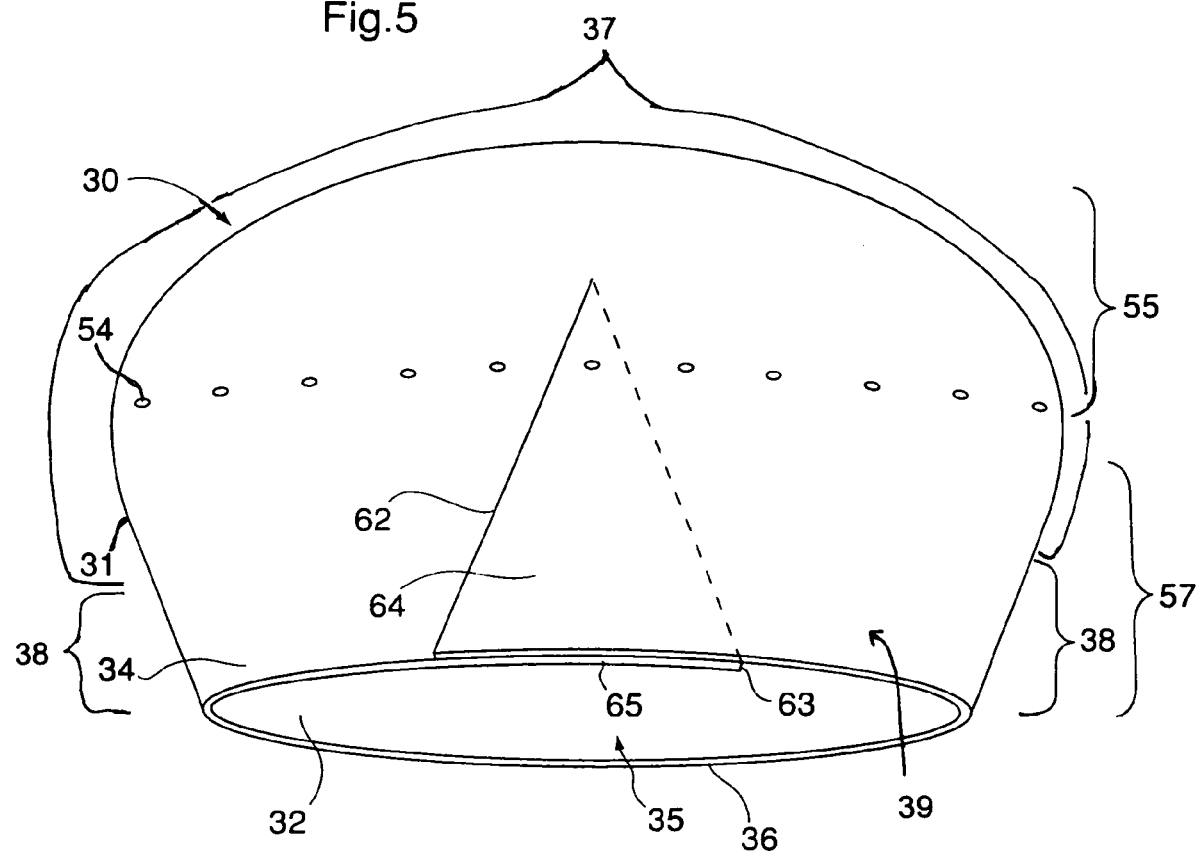
FIG. 5 is a pictorial view of a first embodiment of a prosthesis in accordance with the present invention in a closed configuration it is to assume when applied onto the condyle of the temporomandibular joint shown in FIG. 4.

Reference is made to FIG. 5 which illustrates a preferred embodiment of a prosthesis 30 in accordance with the present invention. The prosthesis 30 comprises a hollow cap-like member with a wall 31 providing an inwardly directed inner surface 32 and an outwardly directed outer surface 34. The prosthesis 30 as a cap-like member has an opening 35 surrounded by edge 36 of the wall 31. In the preferred embodiment, the inwardly directed surface 32 is generally concavely rounded and the outwardly directed surface 34 is a parallel mirror image of the inwardly directed surface 32 and, accordingly, the outer surface 34 is convexly outwardly rounded. The inner surface 32 of the prosthesis 30 is formed to have a shape which is substantially identical to the articular surface 18 of the condyle 15 onto which the prosthesis 30 is to be coupled.

Figure 4:
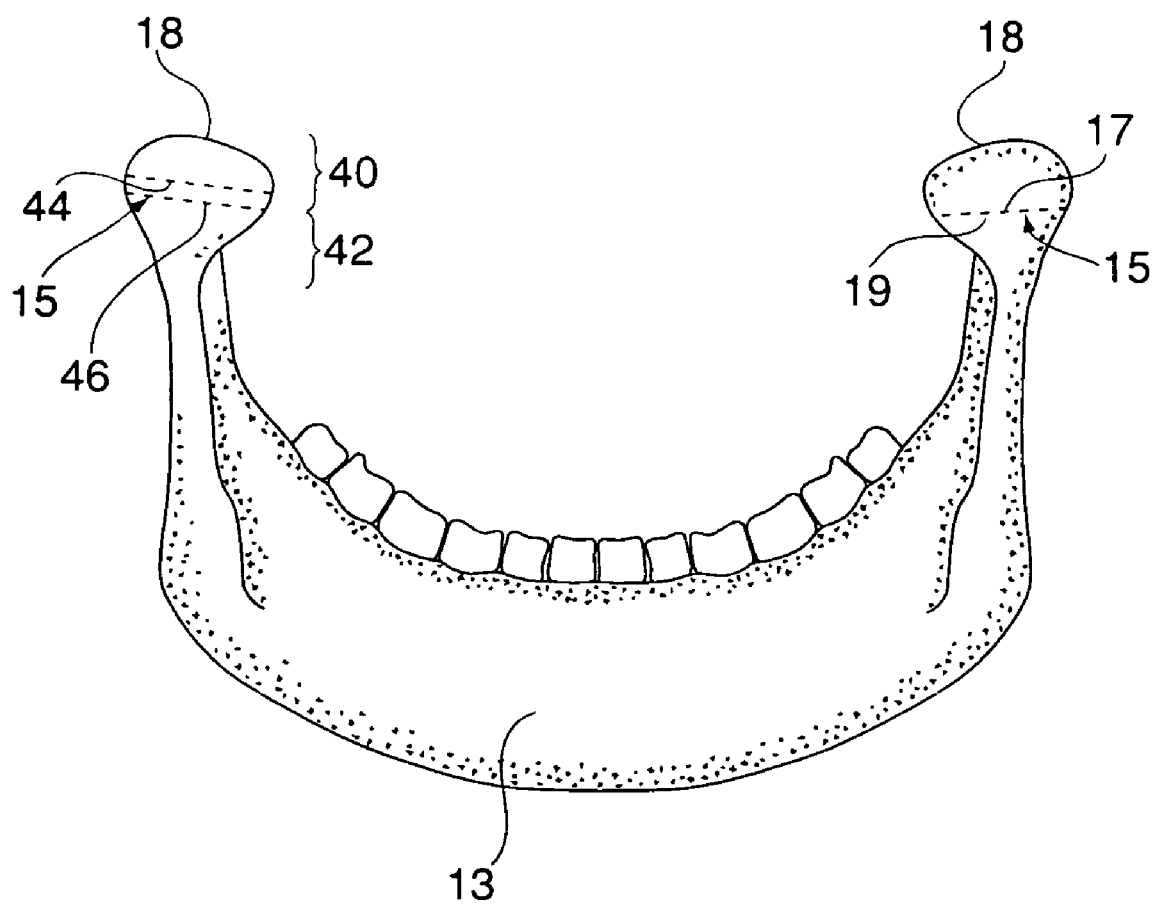
FIG. 4 is a posterior-to-anterior view of a human mandible illustrating the environment of a natural condyle of a temporomandibular joint.

The condyle 15 as seen in FIG. 4 has a bulbous end 40 joined to the remainder of the bone by a neck 42. The bulbous end 40 has portions with larger circumferences than portions of the neck 42. For example, the bulbous end has a largest circumference 44 as indicated by a single dot line, and the neck 42 has a smaller circumference 46 as indicated by a double dot line.

The internal surface of prosthesis 30, as seen in FIG. 5, similarly has a largest circumference at 54 indicated by a single dot line and corresponding to largest circumference 44 of the bulbous end 40 of the condyle 15. The prosthesis 30, as seen in FIG. 5, has a smaller circumference at its opening 35 which corresponds to smaller circumference 46 of the neck of the condyle 15.

The prosthesis 30 is shown in FIG. 5 in a closed configuration which it is to assume when applied over the condyle 15 and which shape it may be formed to inherently adopt. The prosthesis 30 of FIG. 5 is adapted to assume the opened configuration shown in FIG. 6 for insertion of the prosthesis onto the condyle 15, and which opened configuration can represent one configuration which a pre-form of the prosthesis 30 may assume during its manufacture. The opened prosthesis 30 of FIG. 6 has a largest circumference at the single dot line 54 and an inner portion 55 above its largest circumference 54 corresponding to the upper portion of the bulbous end 40 of the condyle 15 above its largest circumference 44.

Figure 6:
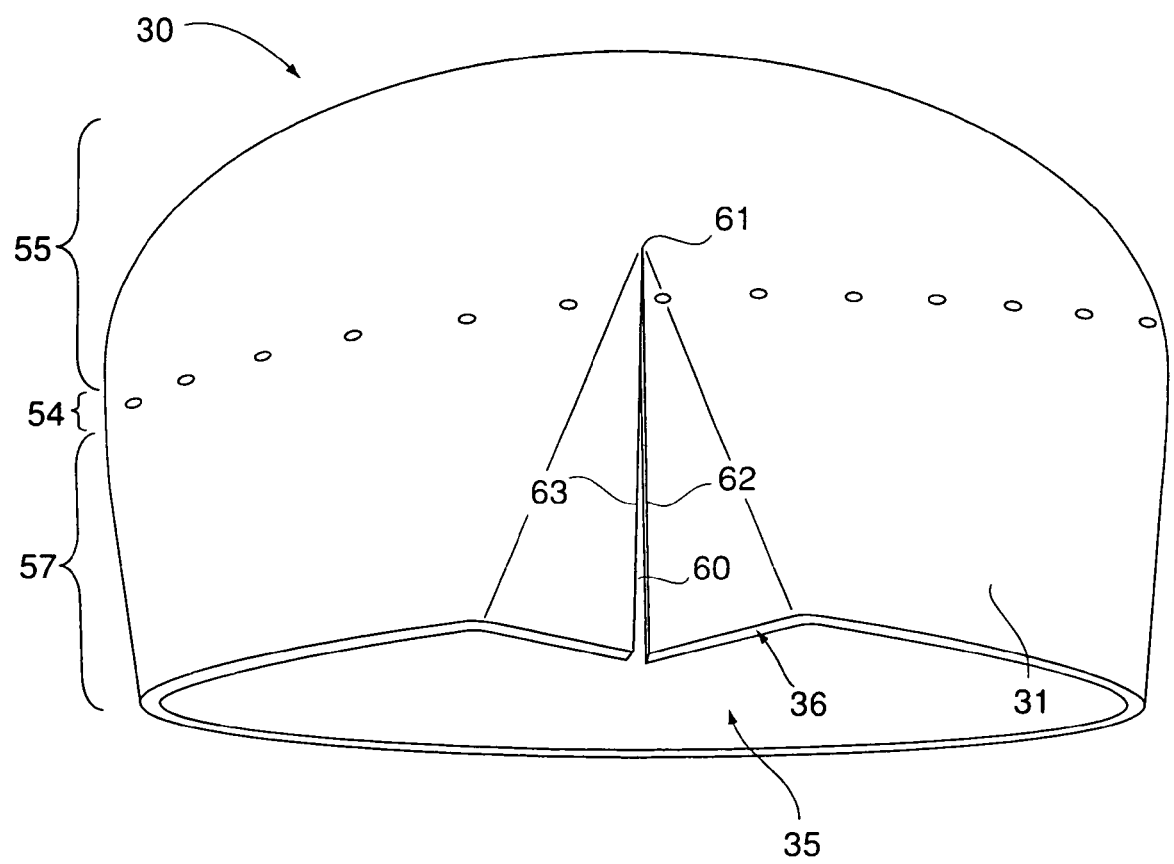
FIG. 6 is a pictorial view of the prosthesis of FIG. 5 in an expanded configuration.

A cut 60 through the wall 31 extends from the edge 36 of the wall 31 inwardly to a point 61 defining two cut edges 62 and 63. Having regard to the circumference of the wall 31 outward of the circumference 54 and the ability of the cut edges 62 and 63 to be moved apart to increase such circumference, the prosthesis 30 of FIG. 6 is adapted to be slid down over the condyle 15 to seat the bulbous end 40 of the condyle 15 in the upper portion 55 of the opened prosthesis 30. Subsequently, the cut edges 62 and 63 may be moved to the closed position of FIG. 5 that is moved circumferentially past each other so that a flap 64 adjacent the cut edge 62 overlies a flap 65 adjacent the cut edge 63, reducing the circumference of a lower portion 57 of the prosthesis 30 to assume the reduced circumferences of the neck 42 of the condyle 15 as at the opening 35 of the closed prosthesis 30 in FIG. 5.

In the embodiment of FIG. 6, the circumference of the prosthesis 30 outward of the largest circumference 54 is generally proximate to that of the largest circumference 54, albeit reducing marginally towards the opening 35.

As seen in FIGS. 7 to 10, the prosthesis 30 is coupled to the mandibular 13 so as to overlie the articular surface 18 of the condyle 15.

The temporomandibular joint is one example of a diarthrodial joint in which contiguous bony surfaces on each of the condyles 15 of the mandibular 13 and the articular surface 24 on the mandibular fossa 20 are each covered with articular cartilage forming the respective outer surfaces or margins of these bone members. Adjacent surfaces of these bone members are non-contiguous surfaces in a sense that they are not normally in contact in a manner to be force transferring through the joint during movement of the joint. In FIGS. 2 and 4, a dashed line 17 schematically illustrates a boundary between the contiguous bony surfaces carrying articular cartilage 18 and non-contiguous surfaces 19 of the mandibular 13.

Figure 7:
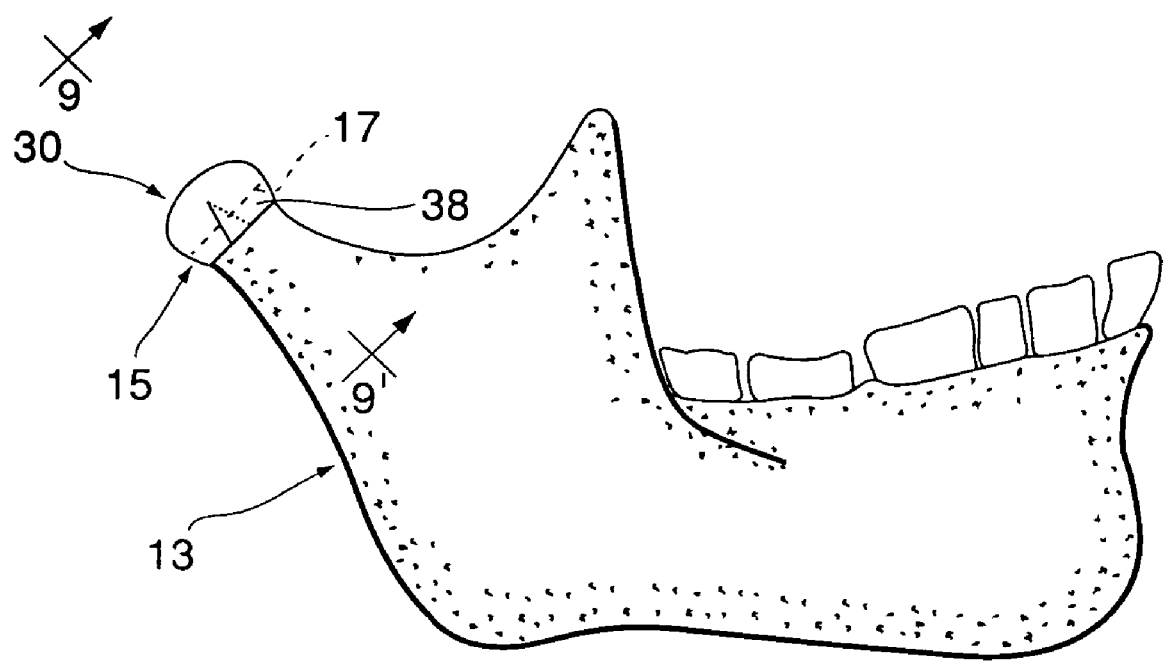
FIG. 7 is an enlarged side view of the mandibular shown in FIG. 3 with the prosthesis of FIG. 5 coupled thereto.
Figure 8:
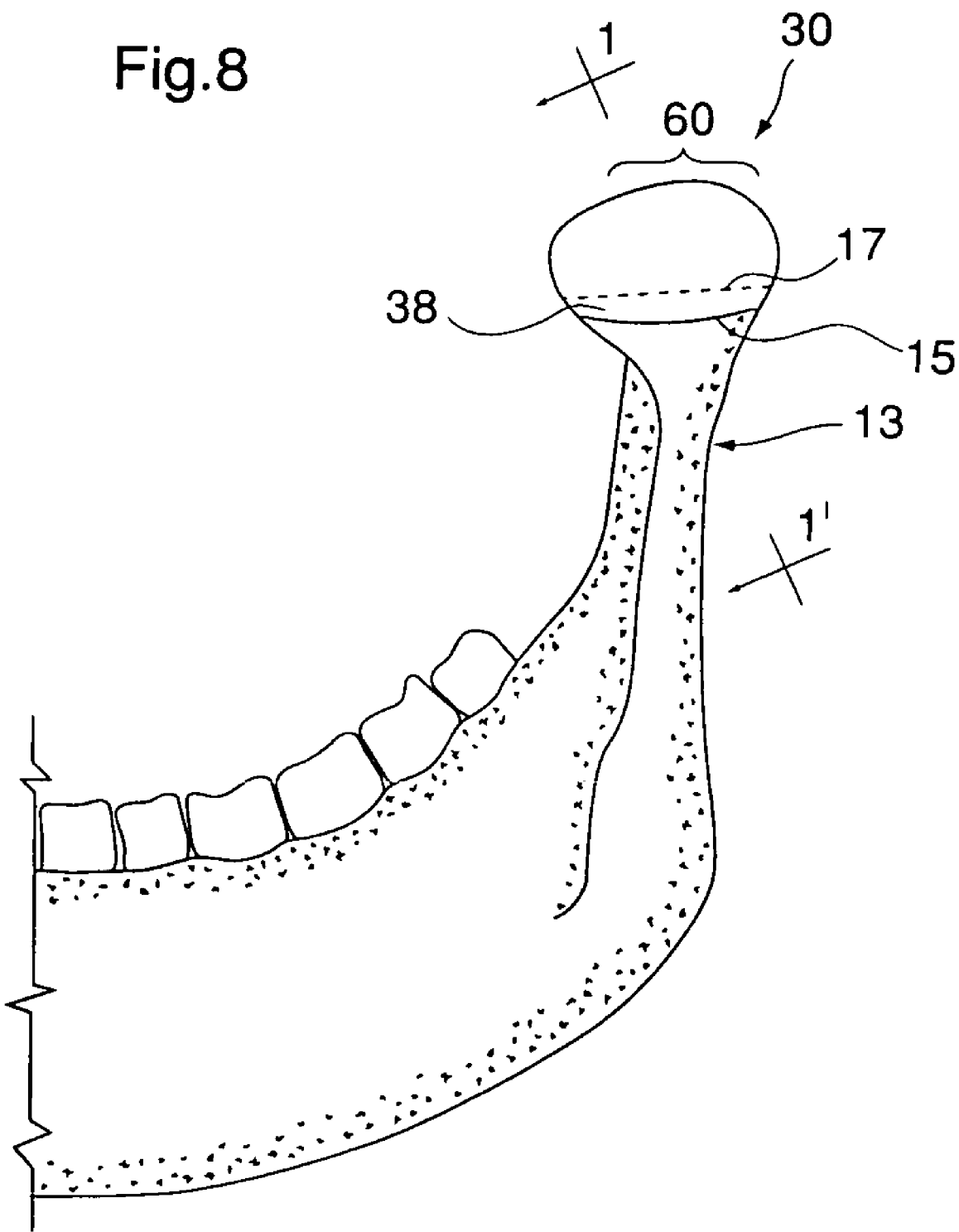
FIG. 8 is an enlarged posterior-to-interior view of the left-hand side of the mandibular shown in FIG. 7 showing the prosthesis applied thereto.

Referring to FIGS. 7 and 8, the prosthesis 30 is shown as applied to the mandibular 13 to substantially entirely cover the outer surface of the articular cartilage 18 of the contiguous bony surfaces, that is, of the condyle 15 on the mandibular 13. The prosthesis 30 includes a coupling portion 38 which, as seen in FIG. 7, extends clearly beyond the articular cartilage 18 and over the non-contiguous surface 19 of the mandibular 13. The prosthesis 30 is marked to indicate the coupling portion 38, as seen in FIG. 5, which is provided over the non-contiguous surface 19 and is of reduced circumference to couple the prosthesis about the neck of the condyle. As is to be appreciated from the FIGS. with the prosthesis 30 applied to the joint, in the resultant modified joint during normal movement of the joint the prosthesis 30 consists the only element foreign to the joint which engages the contiguous bony surfaces on each of the condyle 15 and the mandibular 13; and the prosthesis 30 consists the only element foreign to the joint which is located between the contiguous outer surface of the condyle 15 and the contiguous outer surface of the mandibular 13.

Figure 9:
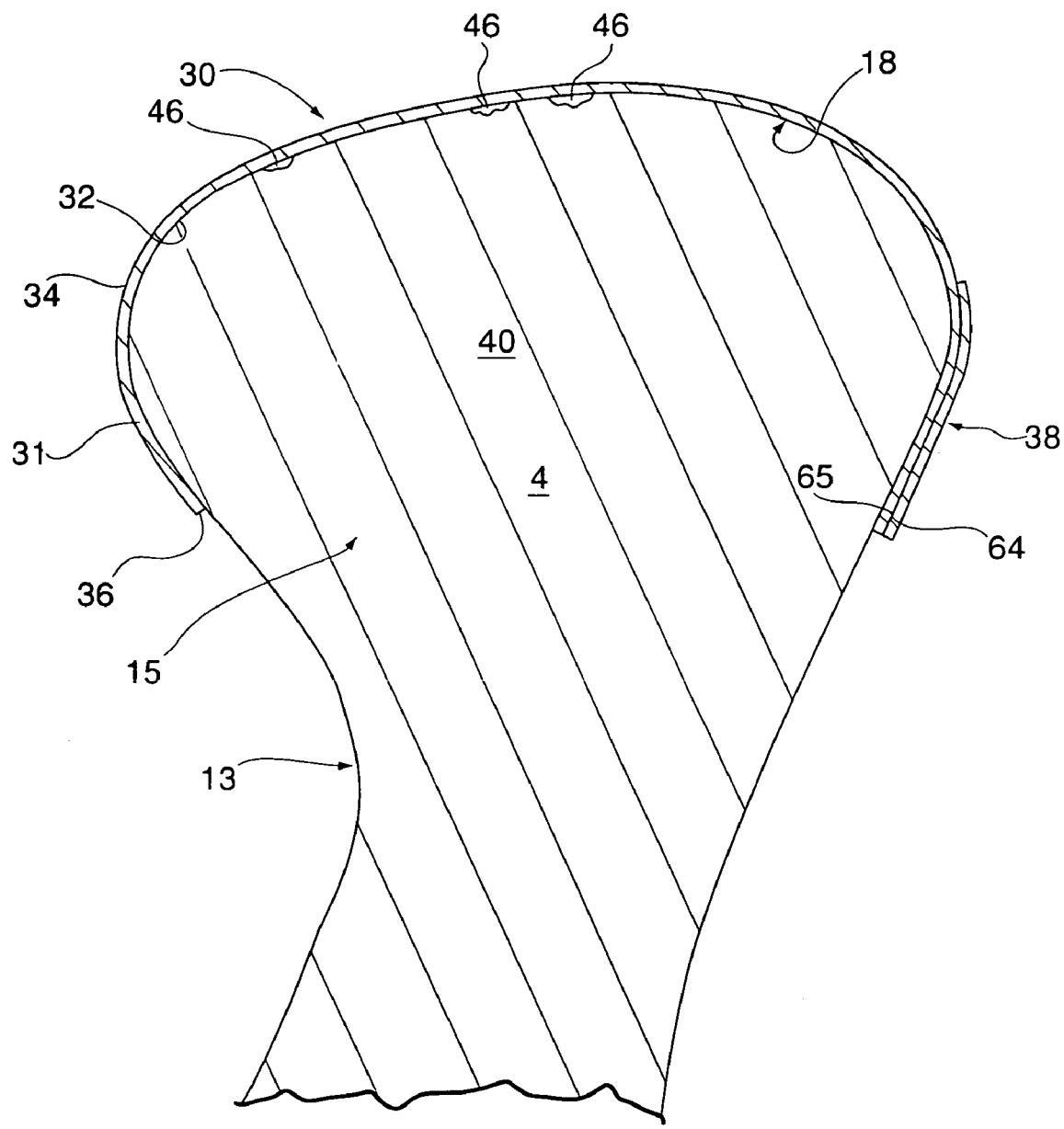
FIG. 9 is a cross-sectional side view along section line 9-9' in FIG. 7.
Figure 10:
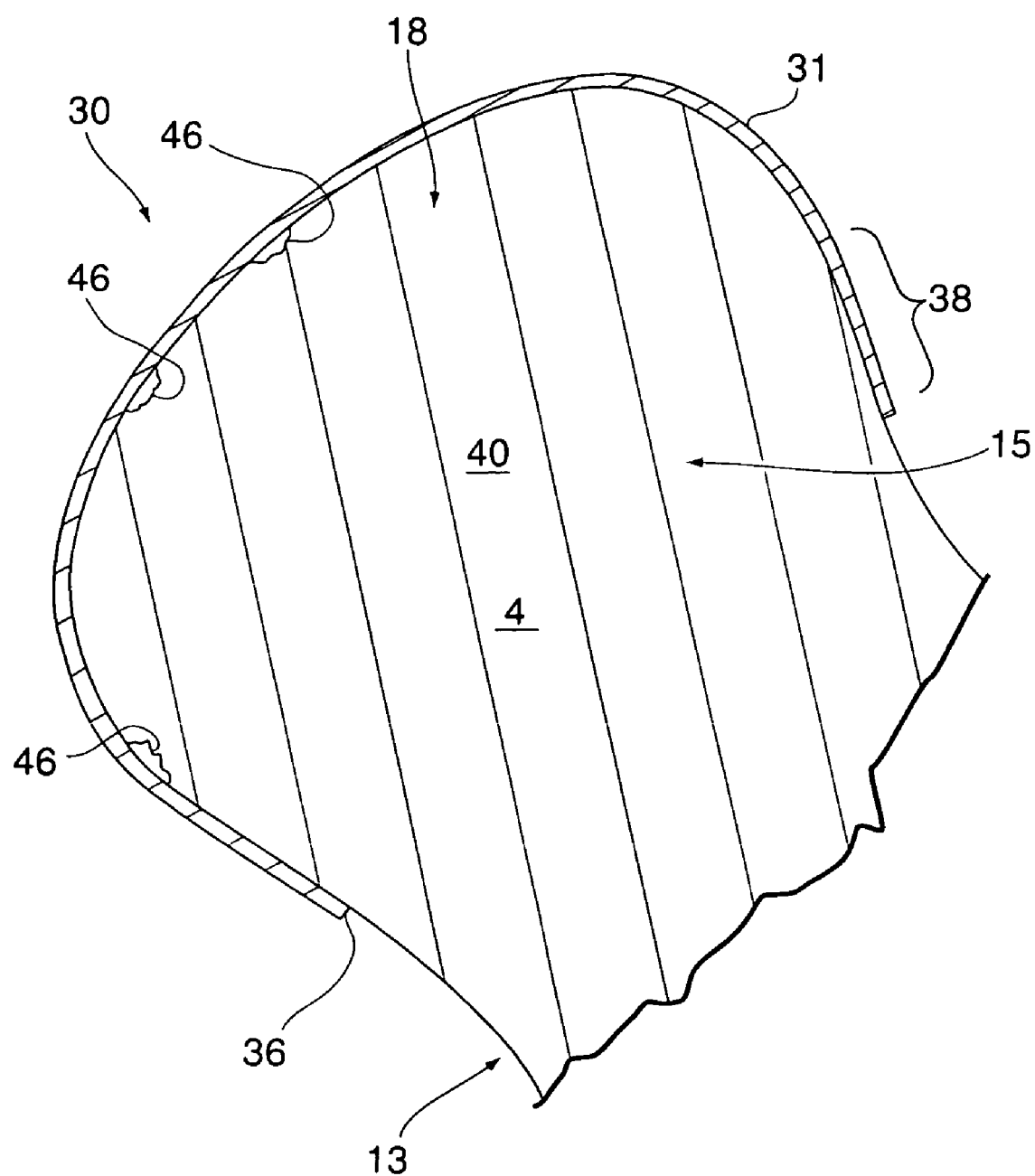
FIG. 10 is a cross-sectional side view along section line 1-1' in FIG. 8.

The prosthesis 30, as best seen in FIGS. 9 and 10, has its interior surface conforming to the shape of the margin, that is, the exterior surface of the articular cartilage 18. FIGS. 9 and 10 schematically illustrates depressions 46 in the articular cartilage 18 as, for example, may be formed due to damage to the cartilage 18. The prosthesis 30 preferably is provided to have a smooth continuous exterior surface 34 which adopts a profile of the articular cartilage 18 assuming that the depressions 46 were not present. The wall 31 of the prosthesis 30 in spanning across the depressions 46 assists in distributing any loading which normally would be applied to the depressions 46 over a greater surface area on the prosthesis 30 and on the surface of the articular cartilage 18.

The prosthesis 30 is preferably formed by a method including scanning the condyle of the mandibular to develop a computerized model of the condyle and notably the shape of the outer surfaces of its articular cartilage and adjacent non-contiguous surfaces. Such scanning may be carried out as by computerized tomography (CT) scans or other imaging techniques.

The computerized model of the condyle may preferably be used to make a physical three-dimensional model of the condyle, placing a foil or sheet of metal over the model and conforming the foil or sheet to adopt the shape of the model. Preferably, a thin sheet of metal as may be commercially available such as tantalum foil of thickness $2/1000^{th}$ of an inch may be manually placed over the model and stretched, formed, thermoformed and/or conformed to the shape of the model, preferably with fold lines or sharp edges minimized, rounded or avoided as far as possible over the contiguous surfaces.

The prosthesis 30 of FIG. 5 comprises a thin sheet member 39 of metal which has been formed over a model of the condyle. FIG. 5 and FIGS. 6 to 14 have not been drawn to scale for ease of illustration, at least in respect of when the thickness of the sheet member 39 is to represent a metal sheet of, say, $2/1000^{th}$ inch.

The prosthesis 30 as illustrated in FIG. 5 may be seen to have its sheet member 39 comprise an interpositional sheath portion 37 of substantially constant width between its inner surface 32 and outer surface 34 adapted to overlie the outer surface of the articular cartilage 18 of the condyle 15 of the mandibular 13 with coupling portion 38 bridging from the sheath portion 37 to overlie non-contiguous surfaces 19 of the condyle 15 adjacent to the articular cartilage 18 thereof and about the reduced circumference neck 42.

The prosthesis 30 may be made as by various processes not limited to making a physical model of the condyle and forming material of the prosthesis over the model. The prosthesis could be made otherwise as by computer controlled machining from a block of metal to have the desired shape and polishing.

The prosthesis 30 is to be secured onto the actual mandibular 13 of a human by a surgical process, namely, open arthrotomy in which the condyle of the mandibular is exposed, the prosthesis is placed over the condyle 15 and secured to the mandibular.

Providing the prosthesis to be made from sheet materials or to have its interpositional sheet portion to be of constant thickness is not necessary. However, providing the thickness of the wall to be of constant thickness is of assistance in achieving the objective of having the outer surface of the prosthesis closely mimic the shape and size of the outer surface of the articular cartilage of the condyle of the mandibular. However, any prosthesis may be adjusted or modified so as to have a wall which may not have a uniform thickness. For example, certain instances may be desirable to provide the prosthesis 30 with increased features of strength, resistance to deformation or resiliency for different portions on the prosthesis. For example, it may be desired to have increased thickness and resistance to deformation over central portions of the articular cartilage and it could be possible as by suitable machining to provide increased thickness over the central end areas without significantly altering the outside surface to have a surface which is different from the shape of the condyle. Such central portions of increased thickness could, having regard to the material of the prosthesis, increase the extent that any forces are distributed over an enlarged area to reduce localizing forces on smaller areas of the articular cartilage. Similarly, the thickness of the wall of the cup-like member proximate its circumferential perimeter for over an area proximate the circumferential perimeter could be reduced in thickness.

Figure 11:
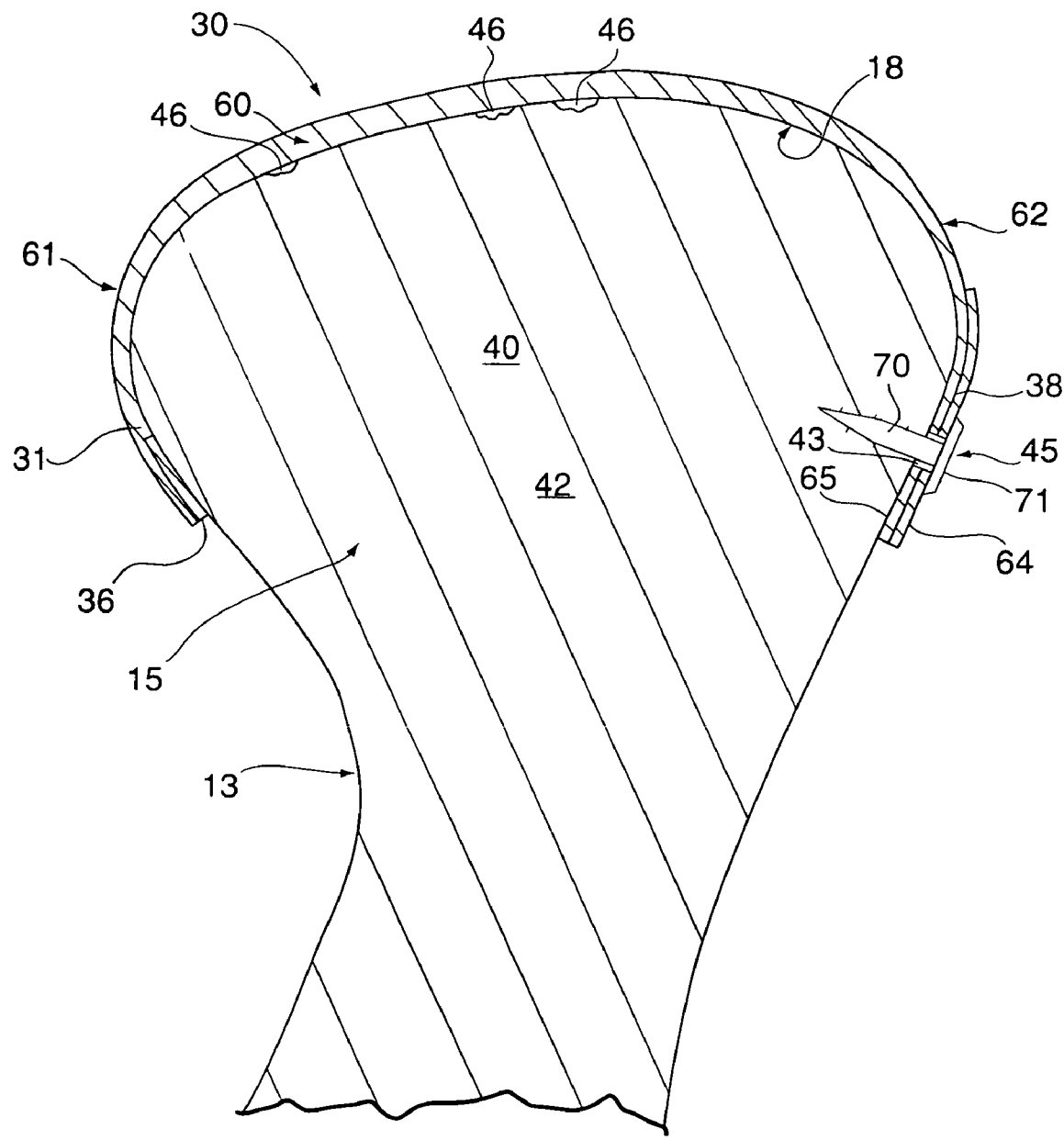
FIG. 11 is a cross-sectional view similar to that in FIG. 9 but with the prosthesis having a central portion of its wall of increased thickness and being additionally secured by a surgical screw.

Reference is made to FIG. 11 which shows a cross-sectional view similar to that in FIG. 9, however, of a modified embodiment of the prosthesis 30. As one modification, the prosthesis 30 has a central portion 60 of its wall of an increased thickness compared to side portions 61 and 62. The increased thickness of the central portion 60 of the wall assists in distributing localized forces applied to areas on either side of the central portion 60 being distributed to enlarged areas as is believed to provide increased protection to the articular cartilage with which the central portion contacts.

As a second modification, aligned holes 43 are provided through the overlapping flaps 64 and 65 and a surgical screw 45 is shown extending through the holes 43 and into the condyle 15 to mechanically fasten the coupling portion 38 of prosthesis to the condyle 15 over its non-contiguous surface. While the screw 45 could be tightened sufficiently to draw the flaps 64 and 65 into the condyle 15 against relative movement, it is preferred as shown that the holes 43 be larger than the shank 70 of the screw 45 and the screw 45 be tightened so as to permit relative sliding of the flaps 64 and 65 underneath the head 71 of the screw 45.

As a third modification, FIG. 11 shows on a lefthand side only the wall 31 at the lower edge 36 bent back underneath itself to provide a reinforced and smooth edge at the edge 36.

Figure 12:
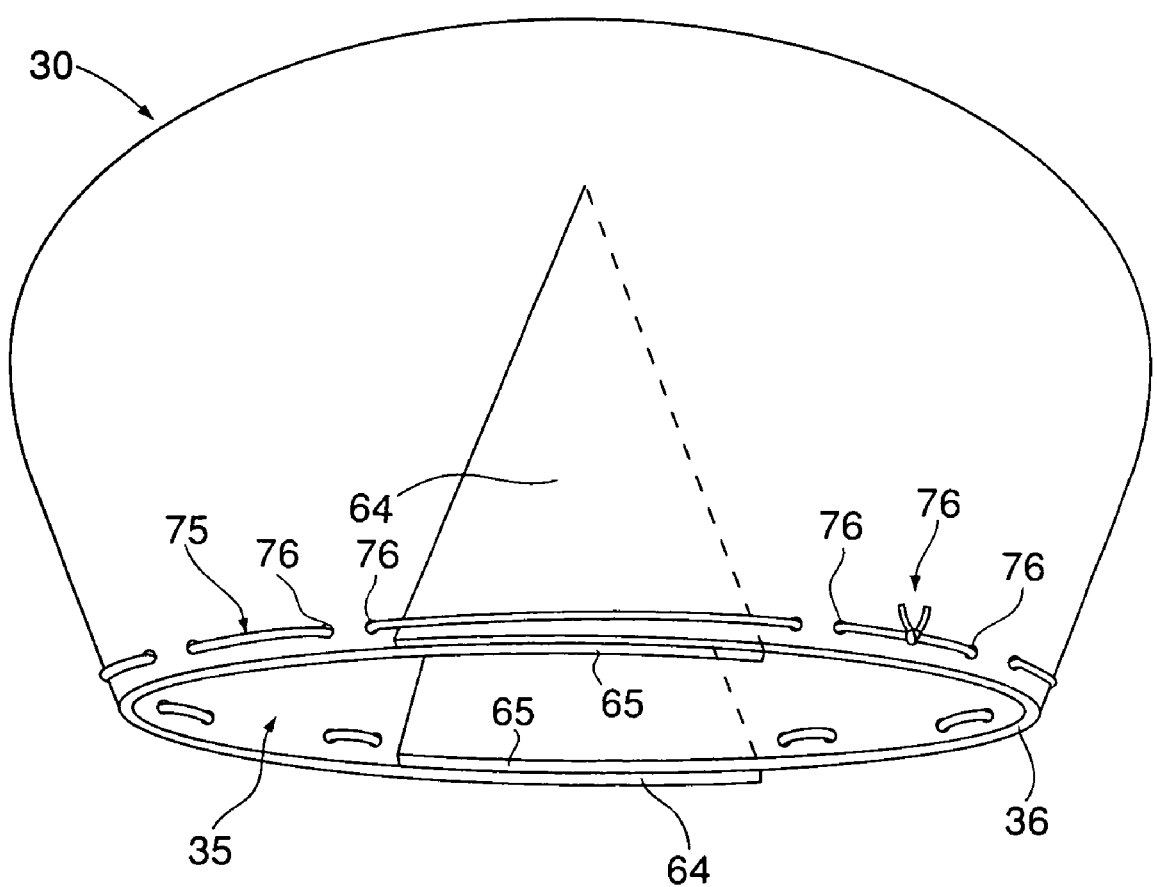
FIG. 12 is a pictorial view of a second embodiment of a prosthesis similar to that in FIG. 5 and including a closing ligature.

Reference is made to FIG. 12 which shows a second embodiment of a prosthesis 30 as in FIG. 5 but modified firstly to provide cut lines and corresponding flaps 64 and 65 on two sides and, secondly, to provide circumferential ligature 75. As seen, a plurality of small spaced eyelet openings 76 are provided circumferentially inwardly from the edge 36 through which the ligature 75 is passed. The ligature may comprise a suture-like string or wire which may have its ends secured together as at 76 to maintain the opening 35 with its reduced circumference. As is to be appreciated from the FIGS. with the prosthesis 30 applied to the joint, in the resultant modified joint during normal movement of the joint the prosthesis 30 and the circumferential ligature 75 consist of the only elements foreign to the joint.

Figure 13:
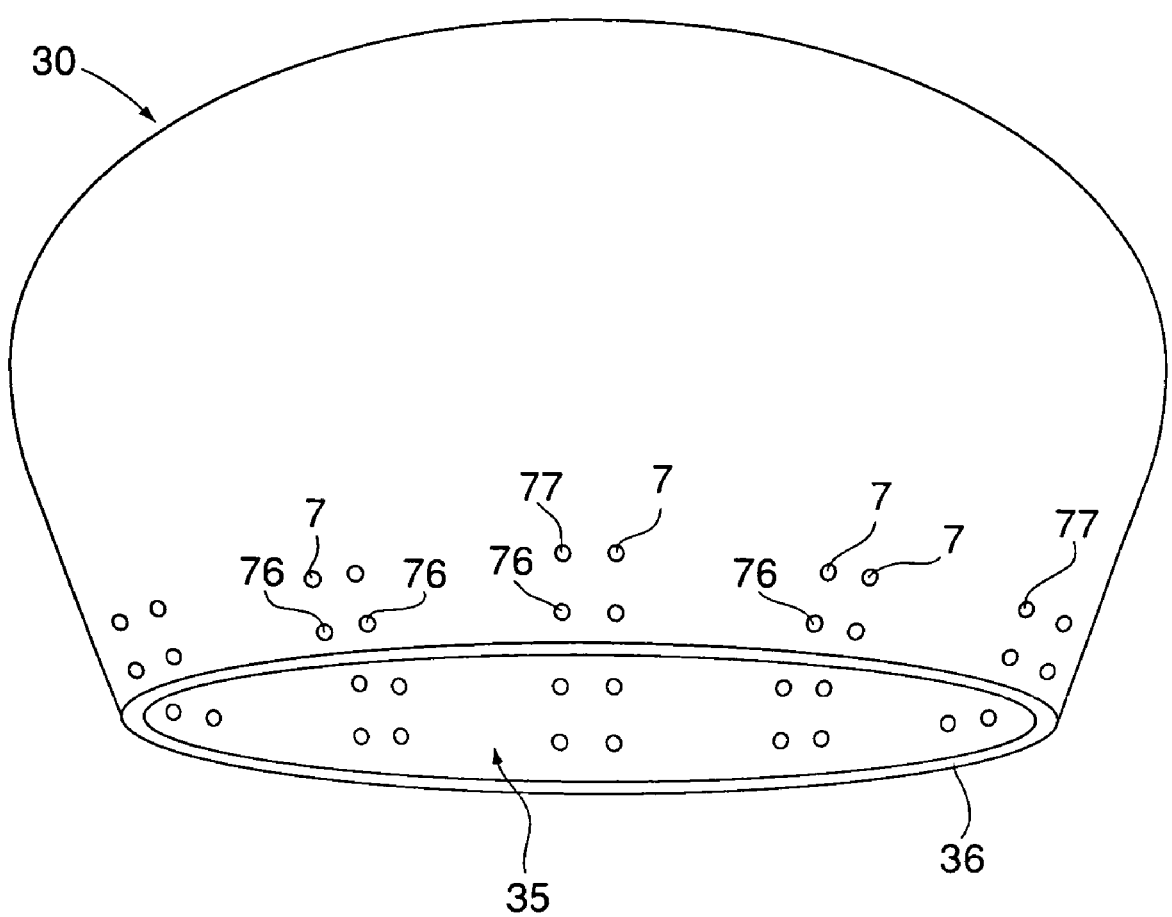
FIG. 13 is a pictorial view of a third embodiment of a prosthesis in accordance with the present invention similar to that in FIG. 5.

Reference is made to FIG. 13 which shows a third embodiment of a prosthesis 30 as in FIG. 5 but modified firstly so as to avoid the cut line and flaps and modified, secondly, to provide two sets of circumferentially extending eyelets 76 and 77 to receive one or more ligatures, not shown, in FIG. 13 but similar to that shown in FIG. 12. The prosthesis of FIG. 13 could be made from materials to be capable of being stretched over its coupling portion 38 for application onto the condyle.

Figure 14:
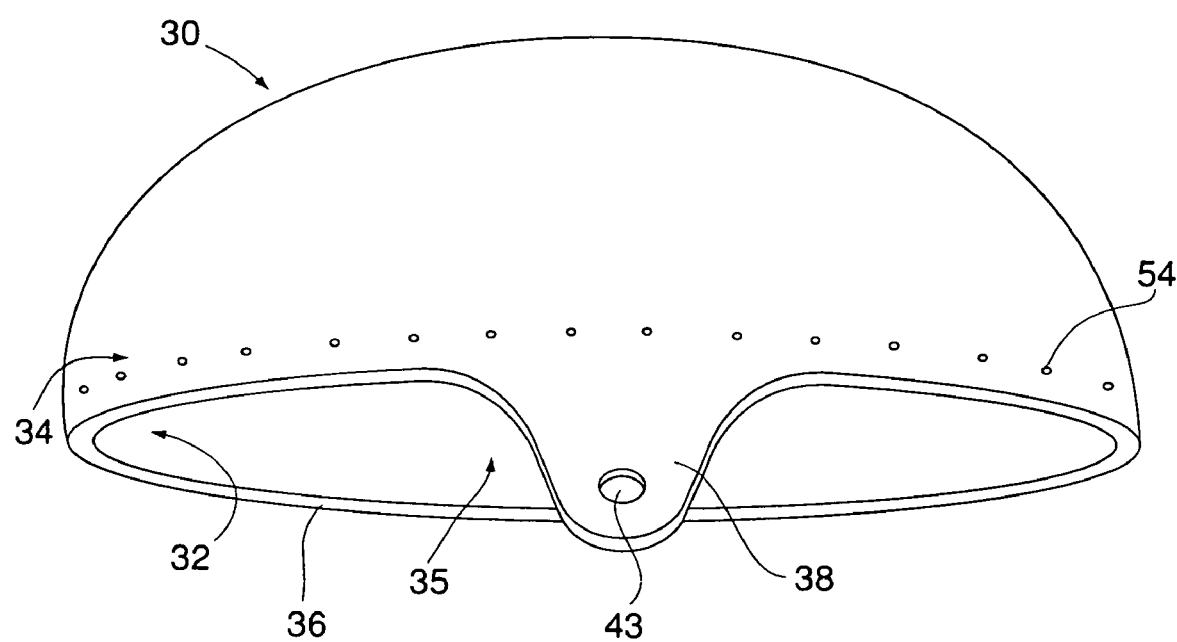
FIG. 14 is a pictorial view of a fourth embodiment of a prosthesis in accordance with the present invention.

Reference is made to FIG. 14 which shows a fourth embodiment of a prosthesis 30 which has its edge 36 about its opening 35 proximate the largest diameter circumference 54 of the prosthesis other than where a tab-like coupling portion 38 extends outwardly to overlie non-contiguous surfaces. A hole 43 through the coupling portion 38 is for coupling to the condyle as with a screw 45 in a manner similar to that shown in FIG. 11. The prosthesis 30 of FIG. 14 has a shape which permits it to merely be placed over the bulbous end 40 of the condyle 15.

Figure 15:
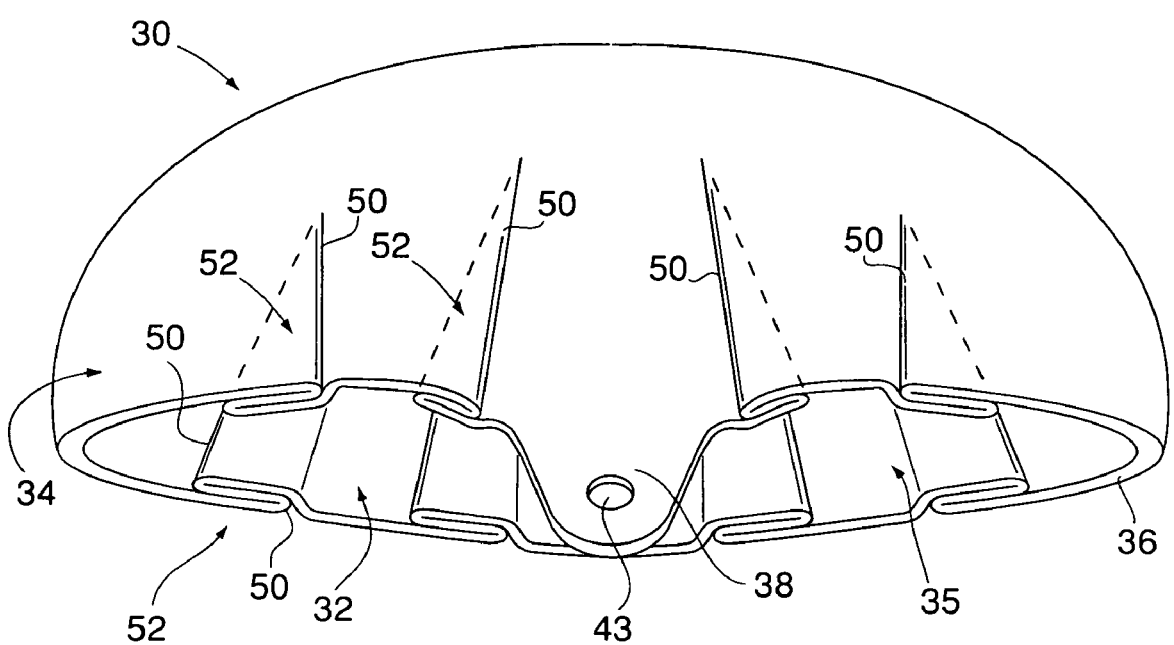
FIG. 15 is a pictorial view of a fifth embodiment of a prosthesis in accordance with the present invention.

Reference is made to FIG. 15 which illustrates a fifth embodiment of the prosthesis 30 substantially the same as the prosthesis shown in FIG. 14 but formed by a process in which a physical three-dimensional model is made of the condyle, placing a foil or sheet of metal over the model and conforming the foil or sheet to adopt the shape of the model. A thin sheet of metal as may be commercially available such as tantalum foil of thickness $2/1000^{th}$ of an inch may be manually placed over the model and conformed to the shape of the model preferably with fold lines or sharp edges minimized or avoided for the extent necessary substantially provided merely over non-contiguous surfaces. Excess portions of the sheet may be trimmed preferably leaving the coupling portions through which the opening is provided. Insofar as the foil or sheet cannot be stretched or deformed to adopt the desired shape, but must be folded, as with darts, then such folds as may be necessary are, as far as possible, arranged to occur over the non-contiguous surface of the mandibular 13 and the folds may be mechanically flattened to provide as uniform and smooth a surface as possible. In FIG. 15, a plurality of fold lines 50 for various spaced darts 52 are shown along the outward lateral sides of the prosthesis 30 which is to overlie at least in part the non-contiguous surface of the mandibular. The prosthesis of FIG. 15 has effectively a constant thickness between its inner surface 32 and outer surface 34 preferably at least where it is to overlie the articular cartilage centrally of the condyle where most of the forces are transferred.

FIG. 12 shows the use of a string-like ligature. Various other forms of ligatures may be utilized which may be separate elements from the element forming the prosthesis or may be integrally formed as part of the prosthesis. For example, the flaps 63 and 64 could have some form of interconnection such as hooks or slot members or, alternatively, ligatures could be formed as integral parts of the prosthesis about its outer end as like one or more circumferentially extending straps for engagement. Various ligatures and straps could be used. Additionally, after the prosthesis, for example, of FIG. 5 is located and placed in the closed position, the overlapping flaps could be secured together as by a mechanical device or bonding by cement or the like.

While the prosthesis is shown as adapted for extending over a single condyle, in various instances such like a knee in which two condyles are provided proximate each other, separate prosthesis could be provided for each condyle or, alternatively, a saddle-like prosthesis could be provided to cover both condyles.

While the invention has been described with reference to preferred embodiments, many modifications and variations of the invention will now occur to persons skilled in the art. For a definition of the invention, reference is made to the following claims.

The invention claimed is:

1. A method of modification of an orthopaedic joint joining a first bone member to a second bone member within a mammalian body to provide a resultant modified joint:

the first bone member having a contiguous outer surface which engages with a contiguous outer surface of the second bone member in normal movement of the joint, the method comprising coupling a spacer member to the first bone member to overlie the contiguous outer surface of the first bone member conforming to the shape of the first bone member with the spacer member disposed in between the contiguous outer surface of the first bone member and the contiguous outer surface of the second bone member, the spacer member consisting of a thin sheet member having an inner surface and an outer surface and a thickness between the inner surface and the outer surface in the range of 0.0005 inches to 0.01 inches, the sheet member consisting of a sheet of metal, wherein the joint is a diarthrodial joint in which the contiguous outer surfaces comprise contiguous bony surfaces on each of the first bone member and second bone member which are each covered with articular cartilage forming the respective contiguous outer surface of the first bone member and second bone member, and wherein the continuous bony surfaces on each of the first and second bone members are surfaces which are in contact during normal movement of the joint, the method comprising placing the sheet member to overlie an outer surface of the articular cartilage of the first bone member conforming to the shape of the outer surface of the articular cartilage of the first bone member, wherein in the resultant modified joint during normal movement of the joint:

(a) the inner surface of the sheet member overlies the outer surface of the articular cartilage of the first bone member in engagement therewith and substantially corresponding in shape to the outer surface of the articular cartilage of the first bone member, and (b) the outer surface of the sheet member facing the outer surface of the articular cartilage of the second bone member and in engagement with the outer surface of the articular cartilage of the second bone member;

wherein the inner surface of the sheet member has a coefficient of friction sufficiently low to facilitate relative movement of the inner surface of the sheet member and the articular cartilage forming the contiguous outer surface of the first bone member in engagement with the inner surface of the sheet member, and wherein the outer surface of the sheet member has a coefficient of friction sufficiently low to facilitate relative movement of the outer surface of the sheet member and the articular cartilage forming the contiguous outer surface of the second bone member in engagement with the outer surface of the sheet member.

2. A method as claimed in claim 1 wherein the first bone member having an adjacent outer surface adjacent to the contiguous outer surface of the first bone member which adjacent outer surface is not normally in contact with the second bone member during movement of the joint, the method including coupling the sheet member to the first bone member with the inner surface of the sheet member to overlie both the contiguous outer surface of the first bone member and the adjacent outer surface of the first bone member with a portion of the sheet member disposed in between the outer surface of the articular cartilage of the first bone member and the outer surface of the articular cartilage of the second bone member.

3. A method as claimed in claim 1 wherein the outer surface of the sheet member substantially corresponding in shape to the outer surface of the articular cartilage of the second bone member.

4. A method as claimed in claim 2 wherein the sheet member is coupled to the first bone member on the adjacent outer surface of the first bone member so as to permit marginal movement of the sheet member relative the outer surface of the articular cartilage of the first bone member without displacement from engagement with the outer surface of the articular cartilage of the first bone member.

5. A method as claimed in claim 1 wherein the contiguous outer surface of the first bone member forms a convexly rounded outer surface over a bulbous end of the first bone member joined to the first bone member by a neck of a reduced circumference than a larger circumference of a portion of the bulbous end, the sheet member overlying the bulbous end and its larger circumference portion and extending circumferentially about the neck so as to couple the sheet member to the first bone member against removal.

6. A method as claimed in claim 5 wherein the sheet member forms a cap-like member over the convexly rounded outer surface and partially onto the neck of the first bone member where the sheet member extends circumferentially about the neck of the first bone member.

7. A method as claimed in claim 4 wherein orthopaedic joint is the orthopaedic temporomandibular joint connecting the mandible bone to the temporal bone at the side of the skull, and the first bone member is the condoyle of the mandible bone.

8. A method as claimed in claim 1 wherein the metal is selected from the group consisting of tantalum, zirconium, titanium and alloys thereof.

9. A method as claimed in claim 1 wherein the sheet member is placed and coupled during open arthroscopic surgery, the sheet member is preformed to have the desired shape of the outer surface of the articular cartilage of the first bone member, the sheet member is collapsed upon itself to permit insertion arthoscopically and uncollapsed within the body after insertion about the outer surface of the articular cartilage of the first bone member.

10. A method as claimed in claim 2 wherein a scan is made of portions of the first bone member including the outer surface of the articular cartilage and the adjacent outer surfaces of the first bone member proximate thereto, a three dimensional model of the scanned portions is made, the sheet member is formed in conformance with the shape of the model.

11. A method as claimed in claim 10 wherein the sheet member has memory such that it returns to the shape of the model when deformed from such shape.

12. A method as claimed in claim 10 wherein the sheet member is a resilient member with an inherent bias to return to the shape of the model when deformed from such shape, and which resists deformation from the shape of the model.

13. A method as claimed in claim 1 wherein the sheet member is coupled to the first bone member so as to permit marginal movement of the sheet member relative the outer surface of the articular cartilage of the first bone member without displacement from engagement with the outer surface of the articular cartilage of the first bone member.

14. A method as claimed in claim 13 wherein the outer surface of the sheet member is smooth and resists bonding of the articular cartilage forming the contiguous outer surface of the second bone member thereto, and the inner surface which is smooth and resists bonding of the articular cartilage forming the contiguous outer surface of the first bone member thereto.

15. A method as claimed in claim 1 wherein the sheet member having an interpositional sheath portion which overlies the outer surface of the articular cartilage of the first bone member conforming to the shape of the outer surface of the articular cartilage and is disposed between the outer surface of the articular cartilage of the first bone member and the outer surface of the articular cartilage of the second bone member, the sheet member further including a coupling portion coupling the sheet member to the first bone member at an adjacent outer surface of the first bone member adjacent to the contiguous outer surface to retain the sheath portion disposed in between the outer surface of the articular cartilage of the first bone member and the outer surface of the articular cartilage of the second bone member.

16. A method as claimed in claim 6 including securing the sheet member about the neck with a circumferential ligature which extends circumferentially around the neck about the sheet member where the sheet member extends circumferentially about the neck.

17. A method as claimed in claim 1 wherein the outer surface of the articular cartilage of the first bone member forms a convexly rounded articular outer surface, the sheet member forms a cap-like member sufficiently over the convexly rounded articular outer surface to assist against relative displacement.

18. A method as claimed in claim 17 wherein the sheet member is coupled to the first bone member so as to permit marginal movement of the sheet member relative the outer surface of the articular cartilage of the first bone member without displacement from engagement with the outer surface of the articular cartilage of the first bone member.

19. A method as claimed in claim 18 wherein the convexly rounded articular outer surface is over a bulbous end of the first bone member joined to the first bone member by a neck of a reduced circumference than a larger circumference of a portion of the bulbous end, the sheet member overlying the bulbous end and its larger circumference portion and extending circumferentially about the neck so as to couple the sheet member to the first bone member against removal.

20. A method as claimed in claim 19 including securing the sheet member about the neck with a circumferential ligature which extends circumferentially around the neck about the sheet member where the sheet member extends circumferentially about the neck.

21. A method as claimed in claim 1, wherein the thickness of the sheet member located between the contiguous outer surface of the first bone member and the contiguous outer surface of the second bone member is a constant thickness.

22. A method as claimed in claim 20 wherein the sheet member consists of a sheet of metal selected from the group consisting of tantalum, zirconium, titanium and alloys thereof and the thickness of the sheet member located between the contiguous outer surface of the first bone member and the contiguous outer surface of the second bone member is a constant.

23. A method as claimed in claim 20 wherein the circumferential ligature is selected from the group consisting of a string member, a strap member and a wire member.

24. A method as claimed in claim 23 wherein the metal is selected from the group consisting of tantalum, zirconium, titanium and alloys thereof.

25. A method as claimed in claim 23, the neck of the first bone member comprising an adjacent outer surface adjacent to the contiguous outer surface of the first bone member which adjacent outer surface is not normally in contact with the second bone member during movement of the joint, the method including coupling circumferential ligature about the sheet about the adjacent outer surface.

26. A method as claimed in claim 25 wherein in the resultant modified joint the sheet member and the circumferential ligature consist of the only elements foreign to the joint.

27. A method as claimed in claim 26 wherein the thickness of the sheet member located between the contiguous outer surface of the first bone member and the contiguous outer surface of the second bone member is a constant thickness.

28. A method as claimed in claim 26 wherein the orthopaedic joint is the orthopaedic temporomandibular joint connecting the mandible bone to the temporal bone at the side of the skull, and the first bone member is the condyle of the mandible bone.

29. A method of modification of a diarthrodial orthopaedic joint joining a first bone member to a second bone member within a mammalian body to provide a resultant modified joint:

the first bone member having a contiguous outer surface consisting of a normally articular cartilage covered contiguous bony surface which engages with a contiguous outer surface consisting of a normally articular cartilage covered contiguous bony surface of the second bone member during normal movement of the joint, the method comprising coupling a spacer member consisting of a thin sheet member to the first bone member with the sheet member to overlie the contiguous outer surface of the first bone member conforming to the shape of the first bone member with the spacer member disposed in between the contiguous outer surface of the first bone member and the contiguous outer surface of the second bone member;

the sheet member having an inner surface and an outer surface and a thickness between the inner surface and the outer surface in the range of 0.0005 inches to 0.01 inches, the sheet member selected from a sheet of metal and a sheet member comprising a composite of plastic or polymer materials with metal providing the inner and outer surfaces as metal, wherein in the resultant modified joint during normal movement of the joint:
(a) the inner surface of the sheet member overlies the outer surface of the articular cartilage of the first bone member in engagement with and substantially corresponding in shape to the outer surface of the articular cartilage of the first bone member, and
(b) the outer surface of the sheet member facing the outer surface of the articular cartilage of the second bone member and in engagement with the outer surface of the articular cartilage of the second bone member;

wherein the inner surface of the sheet member is smooth and has a coefficient of friction sufficiently low to facilitate relative movement of the inner surface of the sheet member and the articular cartilage forming the contiguous outer surface of the first bone member in engagement with the inner surface of the sheet member, wherein the outer surface of the sheet member is smooth and has a coefficient of friction sufficiently low to facilitate relative movement of the outer surface of the sheet member and the articular cartilage forming the contiguous outer surface of the second bone member in engagement with the outer surface of the sheet member, and wherein the sheet member is coupled to the first bone member so as to permit marginal movement of the sheet member relative the outer surface of the articular cartilage of the first bone member without displacement from engagement with the outer surface of the articular cartilage of the first bone member.

30. A method of modification of an orthopaedic joint joining a first bone member to a second bone member within a mammalian body to provide a resultant modified joint: the first bone member having a contiguous outer surface which engages with a contiguous outer surface of the second bone member in normal movement of the joint, the method comprising coupling a spacer member to the first bone member to overlie the contiguous outer surface of the first bone member conforming to the shape of the first bone member with the spacer member disposed in between the contiguous outer surface of the first bone member and the contiguous outer surface of the second bone member the spacer member consisting of a thin sheet member having an inner surface and an outer surface and a thickness between the inner surface and the outer surface in the range of 0.0005 inches to 0.01 inches, the sheet member selected from a sheet of metal and a sheet member comprising a composite of plastic or polymer materials with metal providing the inner and outer surfaces as metal, wherein the joint is a diarthrodial joint in which the contiguous outer surfaces comprise contiguous bony surfaces on each of the first bone member and second bone member which are each covered with articular cartilage forming the respective contiguous outer surface of the first bone member and second bone member, and wherein the contiguous bony surfaces on each of the first and second bone members are surfaces which are in contact during normal movement of the joint, the method comprising placing the sheet member to overlie an outer surface of the articular cartilage of the first bone member conforming to the shape of the outer surface of the articular cartilage of the first bone member, wherein in the resultant modified joint during normal movement of the joint:
(a) the inner surface of the sheet member overlies the outer surface of the articular cartilage of the first bone member in engagement therewith and substantially corresponding in shape to the outer surface of the articular cartilage of the first bone member, and
(b) the outer surface of the sheet member facing the outer surface of the articular cartilage of the second bone member and in engagement with the outer surface of the articular cartilage of the second bone member;
wherein the inner surface of the sheet member has a coefficient of friction sufficiently low to facilitate relative movement of the inner surface of the sheet member and the articular cartilage forming the contiguous outer surface of the first bone member in engagement with the inner surface of the sheet member, and
wherein the outer surface of the sheet member has a coefficient of friction sufficiently low to facilitate relative movement of the outer surface of the sheet member and the articular cartilage forming the contiguous outer surface of the second bone member in engagement with the outer surface of the sheet member, the first bone member having an adjacent outer surface adjacent to the contiguous outer surface of the first bone member which adjacent outer surface is not normally in contact with the second bone member during movement of the joint, the method including coupling the sheet member to the first bone member with the inner surface of the sheet member to overlie both the contiguous outer surface of the first bone member and the adjacent outer surface of the first bone member with a portion of the sheet member disposed in between the outer surface of the articular cartilage of the first bone member and the outer surface of the articular cartilage of the second bone member, wherein the contiguous outer surface of the first bone member forms a convexly rounded outer surface over a bulbous end of the first bone member joined to the first bone member by a neck of a reduced circumference than a larger circumference of a portion of the bulbous end, the neck comprising the adjacent outer surface, the sheet member overlying the bulbous end and its larger circumference portion and extending circumferentially about the neck, the method including securing the sheet member about the neck with a circumferential ligature which extends circumferentially around the neck about the sheet member where the sheet member extends circumferentially about the neck, wherein the circumferential ligature is selected from the group consisting of a string member, a strap member and a wire member.

31. A method as claimed in claim 30 wherein the sheet member having a cap-like member with an opening defined within an edge of the sheet member, the method comprising passing the bulbous end of the first bone member through the opening of the cap-like member to locate the cap-like member over the bulbous end with the edge disposed circumferentially around the neck, and reducing a circumferential extent of the opening proximate the edge about the neck and maintaining the circumferential extent of the opening reduced with the circumferential ligature.

32. A method as claimed in claim 30 wherein the sheet member is coupled to the first bone member so as to permit marginal movement of the sheet member relative the outer surface of the articular cartilage of the first bone member without displacement from engagement with the outer surface of the articular cartilage of the first bone member.

33. A method as claimed in claim 32 wherein the thickness between the inner surface and the outer surface is in the range of 0.001 inches to 0.01 inches.

34. A method as claimed in claim 32 wherein the thickness is in the range of 0.001 inches to 0.003 inches.

35. A method as claimed in claim 1 wherein in the resultant modified joint during normal movement of the joint:
   (c) the sheet member consists the only element foreign to the joint which engages the contiguous bony surfaces on each of the first and second bone members; and
   (b) the sheet member consists the only element foreign to the joint which is located between the contiguous outer surface of the first bone member and the contiguous outer surface of the second bone member.

36. A method as claimed in claim 29 wherein in the resultant modified joint during normal movement of the joint:
   (c) the sheet member consists the only element foreign to the joint which engages the contiguous bony surfaces on each of the first and second bone members; and
   (d) the sheet member consists the only element foreign to the joint which is located between the contiguous outer surface of the first bone member and the contiguous outer surface of the second bone member.

37. A method as claimed in claim 30 wherein in the resultant modified joint during normal movement of the joint:
   (c) the sheet member consists the only element foreign to the joint which engages the contiguous bony surfaces on each of the first and second bone members;
   (d) the sheet member consists the only element foreign to the joint which is located between the contiguous outer surface of the first bone member and the contiguous outer surface of the second bone member, and
   (e) the sheet member and the circumferential ligature consist of the only elements foreign to the joint.

38. A method as claimed in claim 1 wherein the thickness is in the range of 0.001 inches to 0.01 inches.

* * * * *